United States Patent
Truckai et al.

(10) Patent No.: US 10,548,664 B2
(45) Date of Patent: *Feb. 4, 2020

(54) SYSTEMS AND METHODS FOR PERMANENT FEMALE CONTRACEPTION

(71) Applicant: Cirrus Technologies KFT, Budapest (HU)

(72) Inventors: Csaba Truckai, Saratoga, CA (US); Benedek Orczy-Timko, Budapest (HU); John H. Shadduck, Menlo Park, CA (US)

(73) Assignee: Hermes Innovations, LLC, San Jose, CA (US)

( * ) Notice: Subject to any disclaimer, the term of this patent is extended or adjusted under 35 U.S.C. 154(b) by 295 days.

This patent is subject to a terminal disclaimer.

(21) Appl. No.: 15/072,203

(22) Filed: Mar. 16, 2016

(65) Prior Publication Data

US 2016/0270846 A1 Sep. 22, 2016

Related U.S. Application Data

(60) Provisional application No. 62/133,873, filed on Mar. 16, 2015.

(51) Int. Cl.
| | |
|---|---|
| *A61B 18/14* | (2006.01) |
| *A61B 17/32* | (2006.01) |
| *A61B 18/12* | (2006.01) |
| *A61B 18/00* | (2006.01) |
| *A61B 17/42* | (2006.01) |
| *A61B 17/12* | (2006.01) |
| *A61F 6/20* | (2006.01) |
| *A61F 6/22* | (2006.01) |
| *A61B 17/00* | (2006.01) |

(52) U.S. Cl.
CPC .. *A61B 18/1492* (2013.01); *A61B 17/320016* (2013.01); *A61F 6/22* (2013.01); *A61B 17/12* (2013.01); *A61B 17/12031* (2013.01); *A61B 17/12109* (2013.01); *A61B 17/12159* (2013.01); *A61B 18/1206* (2013.01); *A61B 2017/00004* (2013.01); *A61B 2017/4233* (2013.01); *A61B 2018/00291* (2013.01); *A61B 2018/00559* (2013.01); *A61B 2018/00571* (2013.01); *A61B 2018/00577* (2013.01); *A61B 2018/00589* (2013.01); *A61B 2018/00607* (2013.01); *A61B 2018/1435* (2013.01); *A61F 6/20* (2013.01)

(58) Field of Classification Search
CPC ........... A61B 2018/00559; A61B 2018/00571; A61B 2018/00577; A61B 2018/00589; A61B 2018/00607; A61B 17/12; A61B 17/12031; A61B 2017/4233; A61F 6/20
See application file for complete search history.

(56) References Cited

U.S. PATENT DOCUMENTS

| | | | |
|---|---|---|---|
| 3,584,624 A | 6/1971 | de Ciutiis | |
| 5,303,719 A * | 4/1994 | Wilk ................ | A61B 17/32002 128/831 |
| 6,964,274 B1 | 11/2005 | Ryan et al. | |
| 8,048,101 B2 * | 11/2011 | Lee-Sepsick .... | A61B 17/12099 424/489 |

(Continued)

*Primary Examiner* — Michael F Peffley
*Assistant Examiner* — Bradford C. Blaise
(74) *Attorney, Agent, or Firm* — Levine Bagade Han LLP

(57) ABSTRACT

Medical devices and methods for treating and occluding a female patient's fallopian tubes to provide permanent birth control or sterilization.

20 Claims, 12 Drawing Sheets

(56) References Cited

U.S. PATENT DOCUMENTS

| | | |
|---|---|---|
| 2003/0051735 A1 | 3/2003 | Pavcnik et al. |
| 2008/0071269 A1 | 3/2008 | Hilario et al. |
| 2011/0308527 A1 | 12/2011 | Harrington et al. |
| 2012/0109268 A1 | 5/2012 | Baker et al. |
| 2013/0172870 A1 | 7/2013 | Germain et al. |
| 2013/0220336 A1 | 8/2013 | Gopal et al. |

* cited by examiner

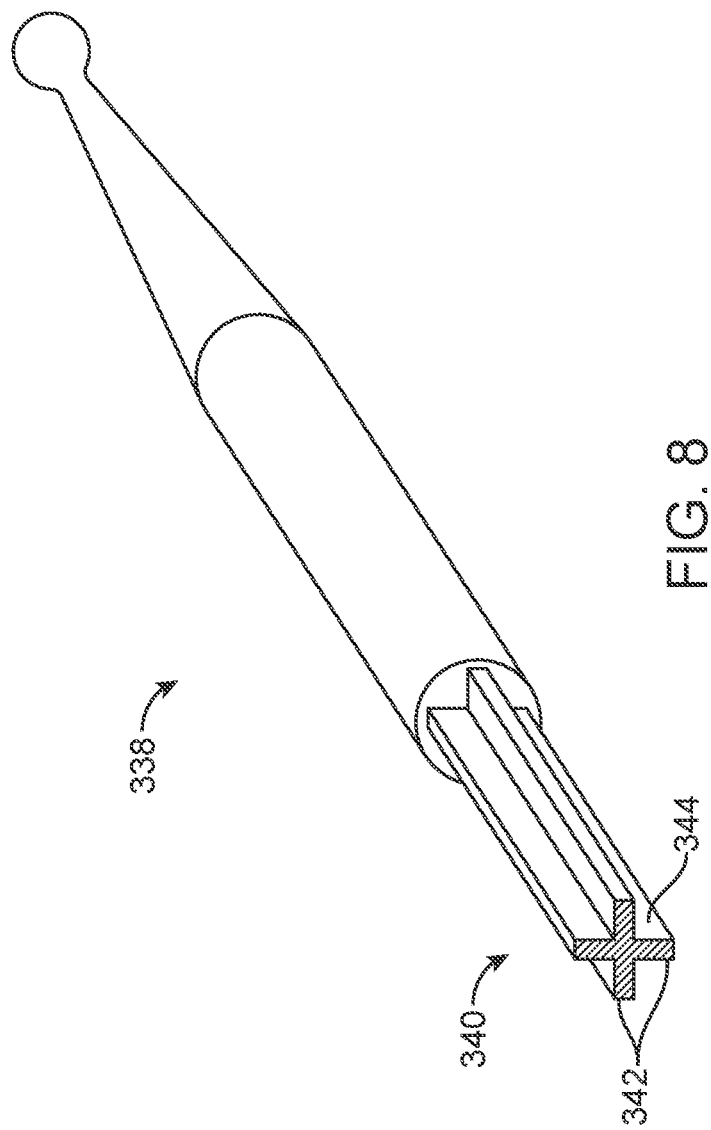

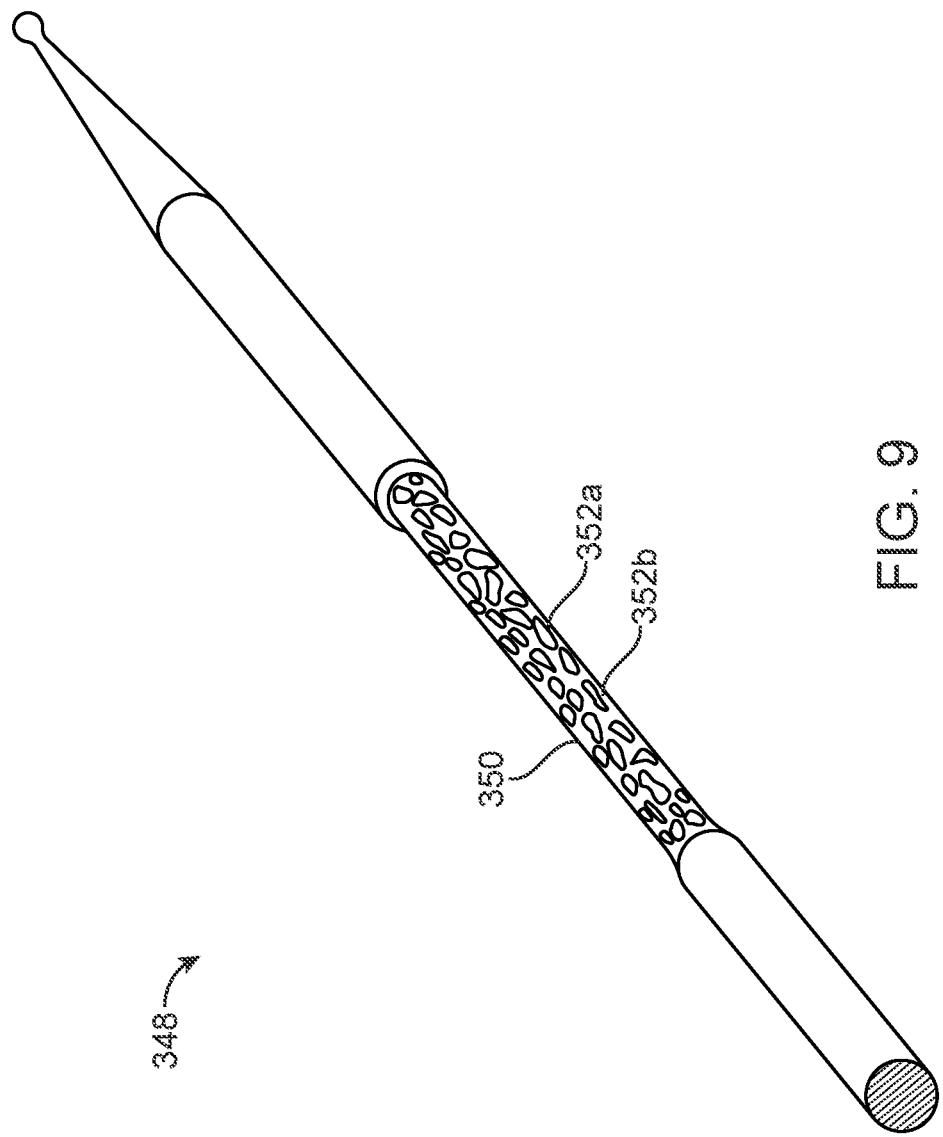

SYSTEMS AND METHODS FOR PERMANENT FEMALE CONTRACEPTION

FIELD OF THE INVENTION

The present invention relates to medical devices and methods for treating and occluding a female patient's fallopian tubes to provide permanent birth control or sterilization.

BACKGROUND

Female sterilization typically involves occluding a patient's fallopian tubes, with various procedures using laparoscopic or minimally invasive trans-cervical approaches. One procedure involves placing flexible coil-like devices into the fallopian tubes, which are made of polyester fibers and metal wires. Tissue in-growth into the implanted devices can block the fallopian tubes. However, such implants are worrisome due to potential unknown long-term effects.

SUMMARY OF THE INVENTION

The present disclosure includes catheter systems and implants together with methods of using such systems and devices for occluding reproductive body lumens such as a female's fallopian tubes. However, the devices and methods can be applied to any body location unless otherwise specifically claimed.

The tubal occlusion procedure described herein is a minimally invasive procedure in which a device can be introduced into the patient's uterine cavity trans-cervically. In one aspect of the method, RF energy ablates a thin layer of tissue in a segment of a fallopian tube. Such treatment can be performed very rapidly, for example in 1 to 60 seconds. A second step involves cutting tissue within the ablated segment to cause bleeding and a subsequent adhesion formation across the coagulated blood. The wound healing response and adhesion of the walls in the segment can permanently close the fallopian tube.

The details of one or more embodiments of the invention are set forth in the accompanying drawings and the description below. Other features, objects, and advantages of the methods and devices will be apparent from the description and drawings, and from the claims.

BRIEF DESCRIPTION OF THE DRAWINGS

FIG. 8 is a sectional view of another variation of a detachable member with a fluted recessed section.

FIG. 9 is a perspective view of another variation of a detachable member with a recessed section comprising first and second different bio-absorbable materials that are absorbed or eroded at different rates.

DETAILED DESCRIPTION THE INVENTION

Figure 1A:
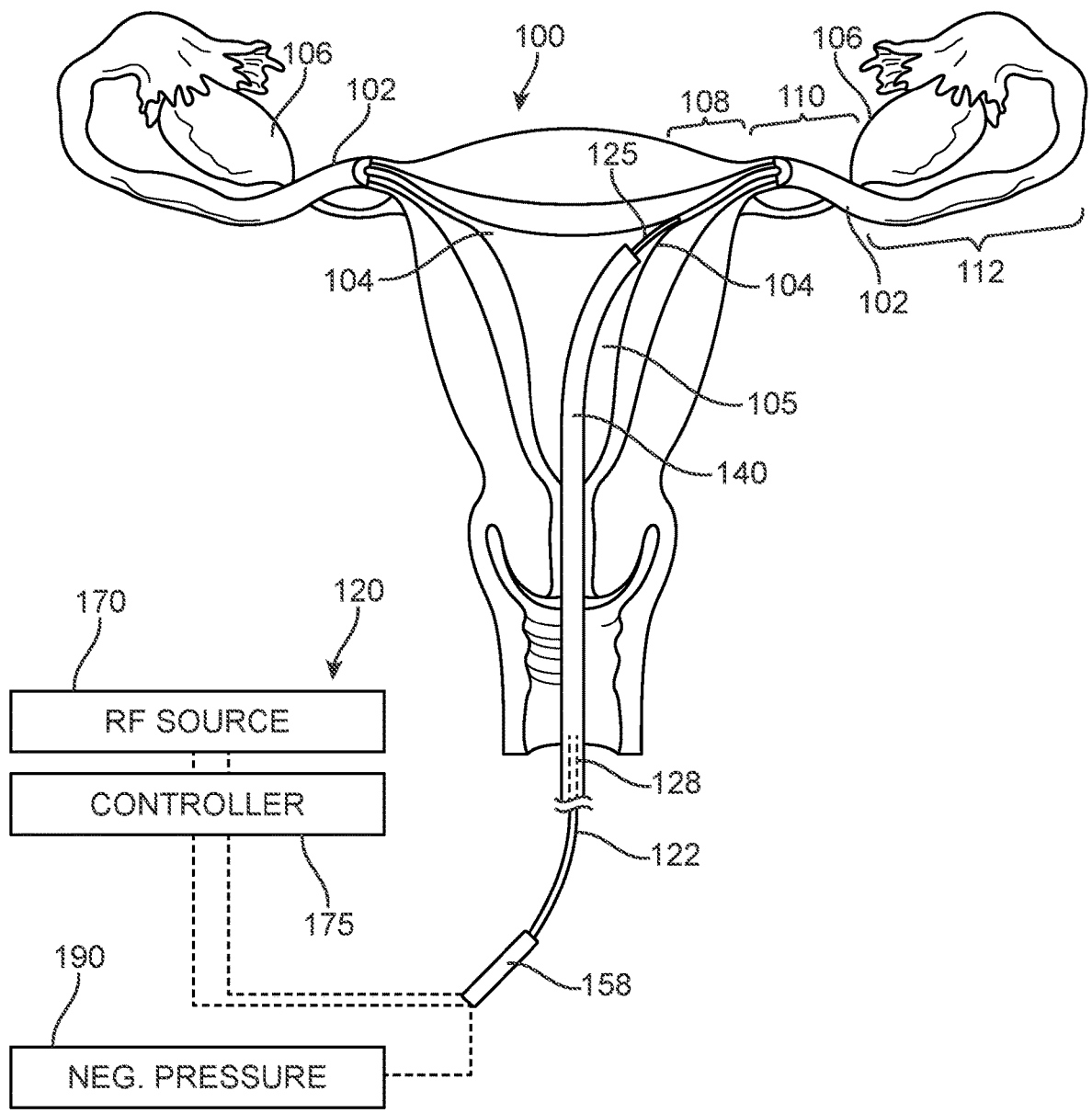
FIG. 1A is a sectional view of a patient's uterus and fallopian tubes showing a variation of a system for occluding a fallopian tube, wherein this variation of the system includes a catheter carrying a detachable bio-absorbable body portion with FIG. 1A illustrating an initial step in a method corresponding to the invention wherein a hysteroscope is introduced trans-cervically into the uterine cavity and the catheter is advanced toward the opening of a fallopian tube.
Figure 1B:
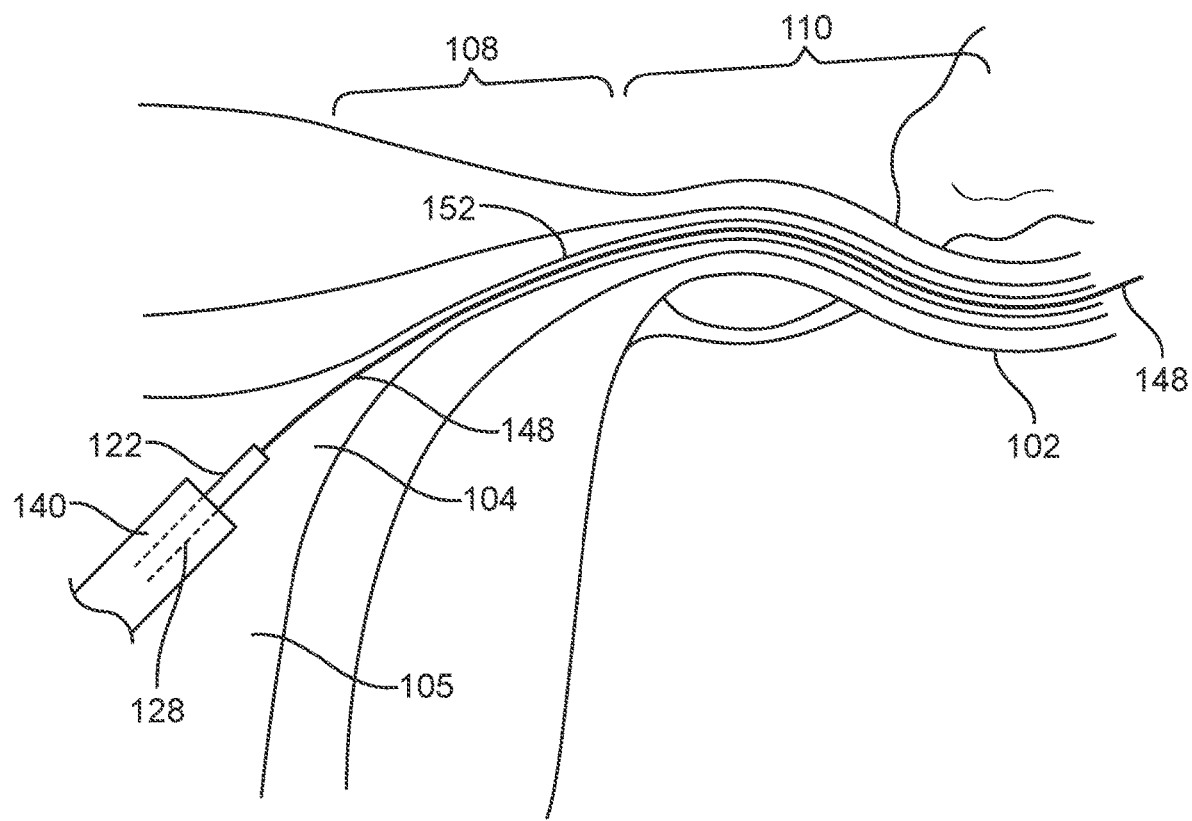
FIG. 1B is an enlarged view of a portion of the uterus and fallopian tube of FIG. 1A illustrating advancing of a guidewire through the catheter and into the fallopian tube.
Figure 1C:
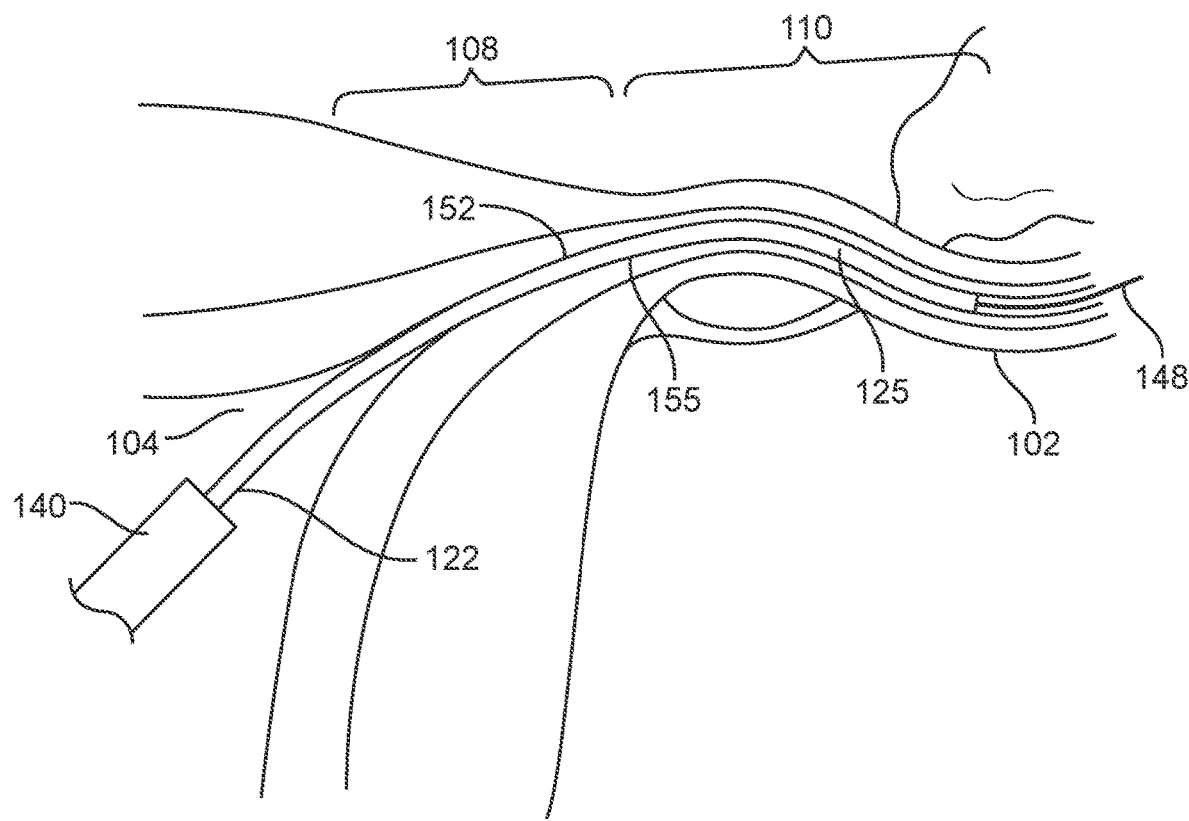
FIG. 1C is a view similar to that of FIG. 1B illustrating a catheter and implant advanced over the guidewire to a targeted site in the fallopian tube.
Figure 1D:
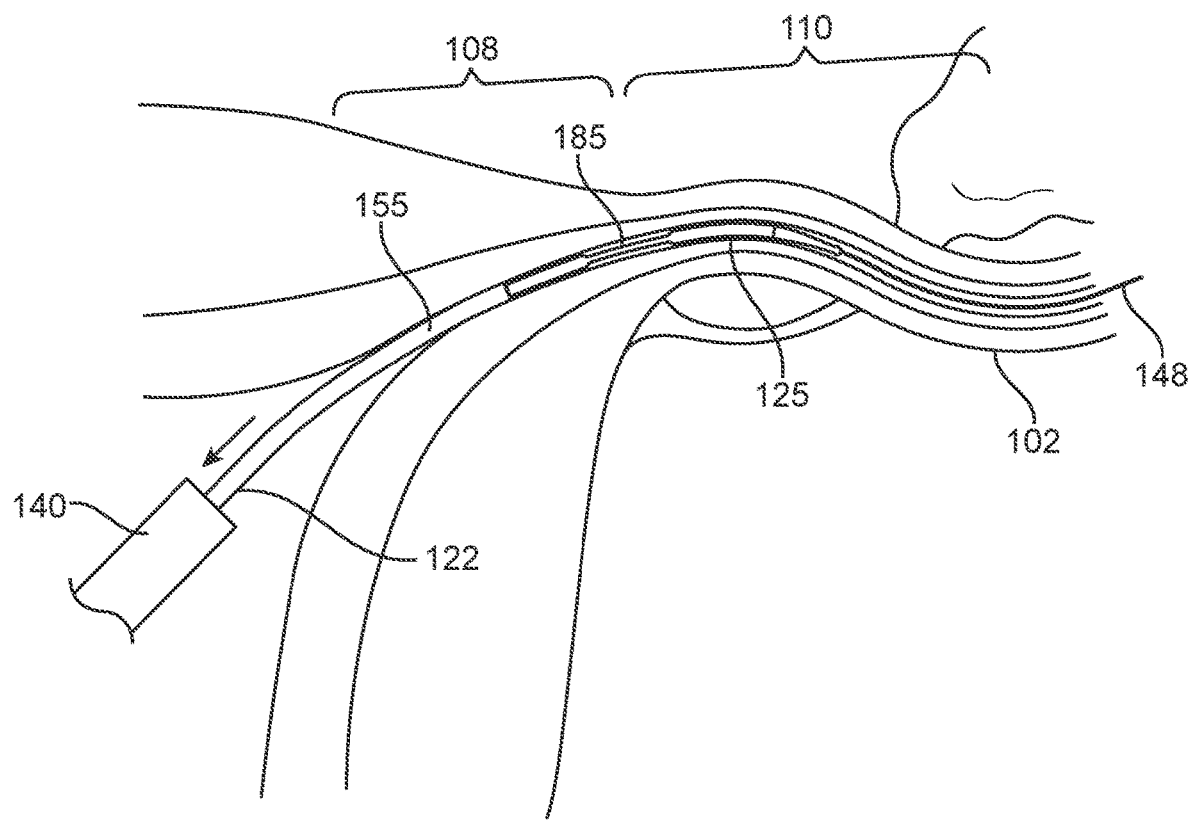
FIG. 1D is a view similar to that of FIG. 1C illustrating retraction of a catheter outer sleeve with a distal blade edge to expose a notched inner member in the targeted site in the fallopian tube.

FIG. 1A illustrates a patient's uterus 100 and fallopian tubes 102 or oviducts, which are paired, tubular conduits that extend from the cornua 104 of the uterine cavity 105 toward the ovaries 106. Each fallopian is about 7 cm to 14 cm in length and is defined by three different sections: the intramural segment 108, the isthmus segment 110 and the ampulla 112 (see FIGS. 1A-1B). The intramural or interstitial segment 108 of the fallopian tube continues from the cornua 104 to the isthmus 110 and is about 1 cm in length with a 1 mm lumen diameter. The isthmus 108 is a round cord-like structure which constitutes the medial one-third of the fallopian tube with a 2 mm to 10 mm outer diameter. The lumen of the fallopian tube is lined with a layer of mucous membrane that can have many folds and papillae. The wall of the fallopian tube includes layers of muscle tissue. The innermost layer has spirally arranged fibers, the middle layer has circular fibers, and an outer layer has longitudinal muscle fibers. These muscle fibers are adapted to cause peristalsis and antiperistalsis in the fallopian tubes.

FIGS. 1A-1D and 2A-2B illustrate a system 120 that includes an elongate catheter 122 that has a working end 125 (FIG. 2A) that includes structure capable of occluding a patient's reproductive lumen such as fallopian tube 102. The catheter 122 can have a suitable length and diameter for extending through the working channel 128 of a hysteroscope or endoscope 140.

In one embodiment shown in FIGS. 1A-1D, the hysteroscope 140 is an articulating endoscope that can be articulated in the uterine cavity 105 to view the entry to the fallopian tubes 102 and direct the catheter into a fallopian tube 102. In another variation, a straight rigid endoscope could be used with an appropriate viewing angle of 5° to 30° together with a catheter or catheter sleeve that can be articulated with an articulating mechanism to assist in directing a catheter working end into a fallopian tube.

Figure 2A:
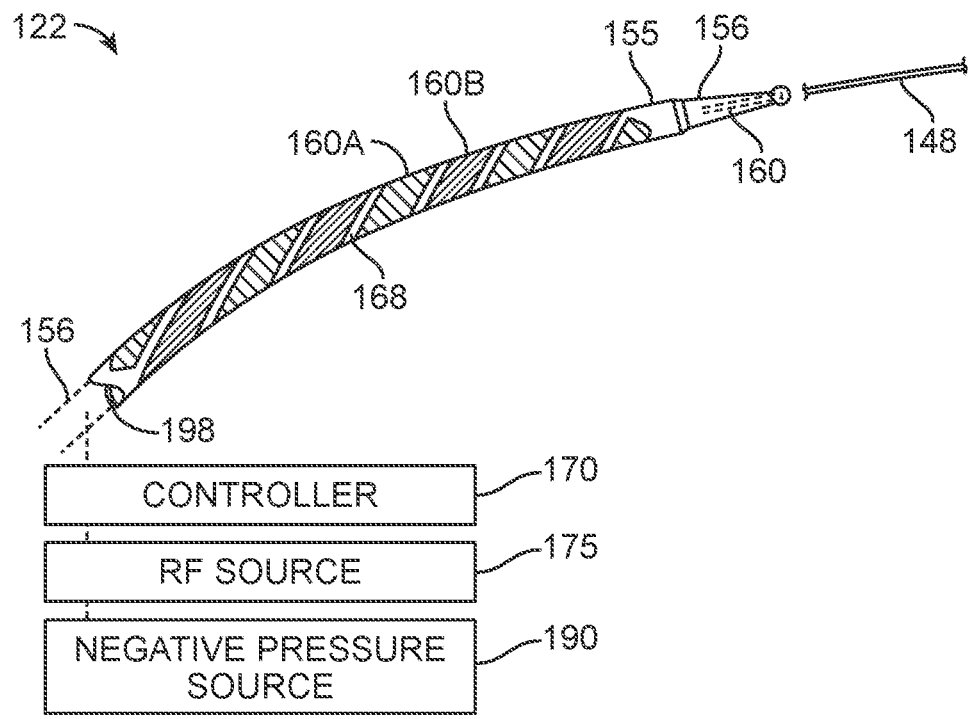
FIG. 2A is a side view of a variation of distal end of the catheter that can be used in the procedure shown by FIGS. 1A-1D and further showing first and second electrodes carried on an exterior surface of the sleeve.
Figure 2B:
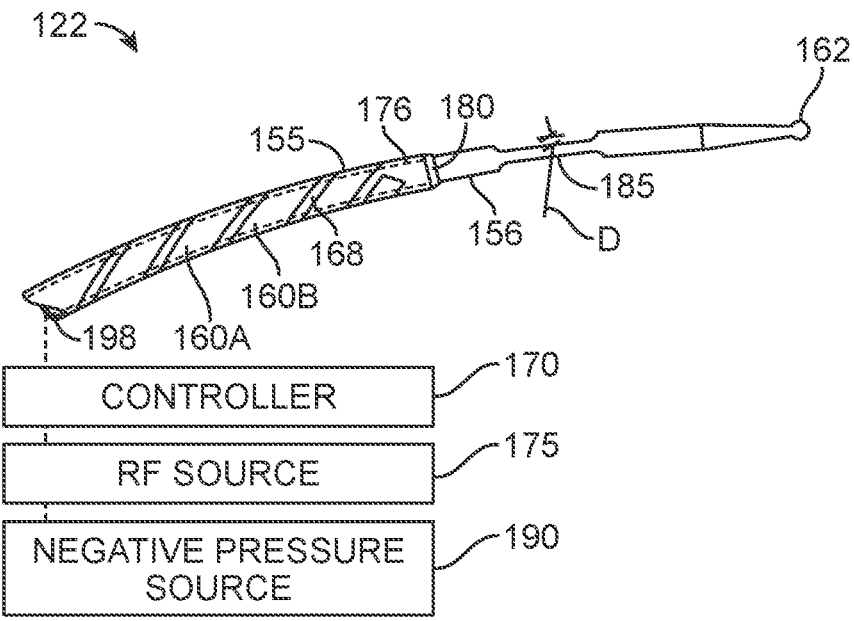
FIG. 2B is a view of the distal working end of the catheter of FIG. 2A with the outer sleeve retracted and further illustrating the blade edge of the outer sleeve and the tissue-receiving notch in the inner member.

In one variation, the catheter 122 as shown in FIGS. 2A-2B includes a guidewire passageway to allow its advancement over a guidewire 148. In general, the variations of catheter working end 125 disclosed herein is adapted to provide functionality in more than one aspect which thus enables the system to effectively occlude fallopian tubes to provide permanent contraception. In one aspect and function, the system and/or implant provide a mechanism to deliver energy to the catheter working end 125 to ablate tissue in the fallopian tube lumen over an elongated segment. As will be described further below, the ablation of endothelial tissue over an elongated segment prevents the rapid re-epithelialization of the lumen, and ablation of underlying muscle layers prevents peristalsis which otherwise could move or disrupt coagulum described next. In additional variations, energy applied to the tissue at the site targeted can result in coagulation, irritate, heating, cooling, and/or result in additional modification of the tissue.

In a second aspect, the system and working end 125 are adapted to resect or cut tissue in the treated segment of the fallopian tube lumen 152 to cause bleeding and coagulation therein. As will be described further below, such bleeding and coagulum at a targeted site in the fallopian tube lumen 152 can improve conditions for fibrosis and adhesion formation in the targeted site to provide a permanent occlusion.

In a third aspect described in some variations below, the working end 125 includes a bio-absorbable detachable body portion that can remain in the fallopian tube over a short (or long) time interval in which it is absorbed or eroded so that no foreign body remains intact in a fallopian tube. The detachable portion can include one or more structures that resist movement of the detached portion within the fallopian tube 102. The such structures can include, but are not limited to the overall expanded or serpentine shape of the body and/or barb-like features on the detached body portion. The detachable body portion further provides a mechanism for blocking or preventing displacement of coagulum that resulted from the bleeding to allow time for the adhesion to fully develop across to coagulum.

In a fourth aspect described in some variations below, a detachable portion of the working end 125 can include a bio-absorbable, bio-degradable or bio-erodible material that includes a very thin plating of a copper powder. In one variation, the selected amount of copper that remains after absorption of a polymeric base material can contribute to permanent contraception.

In a fifth aspect described in some variations below, the copper composition can comprise a bio-erodible electrode that can be coupled to an electrical source to apply the ablative energy to fallopian tube 102 as described above.

Now turning to FIGS. 2A-2B, the working end 125 of the catheter assembly can be described in more detail.

In FIGS. 2A-2B, it can be seen that the catheter 122 has a thin wall outer sleeve 155 that can be moved back and forth and/or rotated over an inner member 156 of the catheter assembly. Both the outer sleeve 155 and the inner member 156 can be fabricated from one or more polymeric materials that are very flexible to allow navigation of the assembly through a fallopian tube. In one variation, the catheter assembly can have a diameter ranging between 1 mm to 3 mm over a distal portion of the catheter that is inserted into the fallopian tube 102. The catheter can have a larger diameter (e.g., 3 mm to 6 mm) extending from its handle 158 (FIG. 1A) toward the working end 125 and then step down to a smaller diameter for the distal portion that is adapted for insertion into a fallopian tube 102.

In another variation, the catheter assembly can have a passageway 160 to allow advancement over or with a guidewire 148 (FIG. 2A) or microcatheter. The guidewire 148 can have a highly flexible tip portion adapted for negotiating through a tortuous path of a fallopian tube and a stiffer portion proximal to the highly flexible portion that can function to straighten the fallopian tube.

In the variation shown in FIG. 2B, the catheter 122 can have its own highly flexible tip 162 (see FIGS. 2A-2B) and thus the catheter working end may be navigated in a fallopian tube lumen 152 without the use of a guidewire.

FIGS. 2A-2B further illustrate an energy delivery component of the system wherein outer sleeve 155 carries opposing polarity bi-polar electrodes 160A and 160B that are operatively coupled to RF source 170 and controller 175. In FIG. 2A, it can be seen that the outer sleeve 155 has first and second opposing polarity electrodes 160A and 160B extending over the portion of the working end 125. The electrodes are shown in a helical configuration and it should be appreciated that the electrode can be any suitable width and extend helically in a tight spiral or a slower pitch or the two electrodes can extend axially on each side of the sleeve 155 with a space therebetween. In one method of making the electrodes, the outer sleeve can be electrolessly plated with gold or copper, and then gaps in the metallic plating can be removed (or a mask can be used) to thus provide the two spaced apart electrodes. The gap 168 between the electrodes can be from 0.1 mm to 1 mm and the electrode width can be from about 0.1 mm to 5 mm. The electrodes 160A-160B can extend over a length of the working end ranging from 1 cm to 5 cm. In other variations, the electrodes can have any form or pattern, including circular, linear, dotted, fragmented or concentric in an outer sleeve 155. In operation, the RF source 170 can be actuated at a suitable power level for about 5 seconds to 1 minute to ablate tissue in the fallopian tube lumen. In one variation, the mucosal layer is ablated over the length of the implant which can be from 1 cm to 3 cm. In this variation, the duty cycle of RF energy delivery can further ablate the underlying circular, longitudinal and spiral muscle layers, which can be a depth of about 0.25 mm to 1 mm. The ablation of the muscle fibers over an elongated segment then will prevent peristalsis and antiperistalsis and thereby assist in preventing displacement of blood and/or coagulum. As noted above, application of energy can also coagulate, heat, cool, or otherwise affect the muscle fibers to achieve the desired result.

FIGS. 2A-2B further illustrate a mechanism carried by the catheter working end 150 that can be actuated to cause bleeding at the site. In one variation as can be understood in FIG. 2B, it can be seen that the distal end 176 of the outer sleeve 155 is a thin blade edge 180, for example of ribbon stainless steel of the type used in a razor blade except of even thinner material. In FIG. 2B, when the outer sleeve 155 and blade edge 180 is moved distally over the recesses or notches 185 in the inner member 156, fallopian tube tissue pressed into the recesses 185 will be cut. The depth D of the recesses 185 is similar to the depth of ablation, so that the cutting depth after one or more passes of blade edge 180 over the recesses 185 will cause bleeding and thus result in the accumulation of coagulum in the treated site. In any event, the blade edge 180 can be reciprocated manually or by a motor drive to cut tissue to a greater depth that of the ablation depth to insure bleeding through any ablated layer. During the cutting procedure, the catheter assembly or the outer sleeve 155 only can be rotated to better cut tissue in 360° around the site. The rotation and reciprocation of the sleeve 155 can be accomplished manually or by a motor drive in the catheter handle 158 (FIG. 1A).

Figure 3:
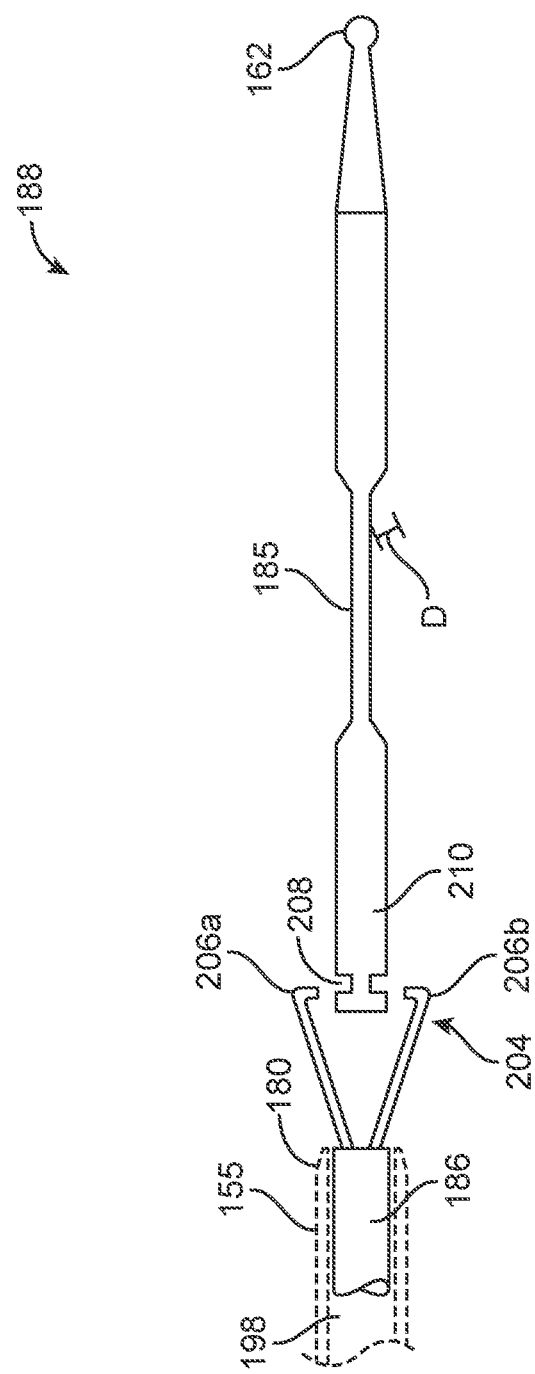
FIG. 3 is a side view of a detachable distal body portion of a catheter inner member of the type shown in FIG. 2B further showing a coupling mechanism.

FIG. 3 illustrates the inner member 156 comprises a proximal body portion 186 and a detachable body portion 188 which can remain in the fallopian tube lumen following the step of cutting tissue described above. In one aspect of the method of the invention, the detachable portion 188 functions to occlude the lumen temporarily to thereby maintain blood and coagulum in a fixed location in the lumen which, in turn, assists in formation of an adhesion. The detachable portion 188 can comprise a polymer adapted to be absorbed or eroded within a range of about 1 day to two weeks. In one variation, the detachable portion 188 has perforated or microporous section that comprises the recesses or notches 185. The porosities fill with blood and coagulum which again assists in accelerating adhesion across the lumen and can also accelerate bio-absorption of the detachable portion. In an embodiment described herein, the polymer detachable body portion 188 can comprise a bio-absorable material. Such materials are well known in the art and can be described as bio-resorbable, bio-absorbable, bio-erodible or bio-degradable and can be assimilated by the body at predictable rates. Bio-resorbable or bio-degradable polymers include polylactic acid (PLA) polyglycolic acid (PGA), polydioxanone (PDS), polyhydroxybutyrate (PHB), polyhydroxyvalerate (PHV), polycaprolactone, polycyanocrylates, or polyphosphazenes. As used herein, the terms bio-absorbable, bio-resorbable and bio-erodible are used interchangeably and include any suitable biocompatible material, mixture of materials or partial components of materials being degradable into other generally non-toxic materials by an agent present in biological tissue, for example by being bio-degraded or being removed by cellular activity, by bulk or surface degradation, or a combination of one or more of the mechanisms of being bio-degraded, bio-eroded, bio-absorbed or bio-resorbed.

In this variation, the detachable body portion 188 can be fabricated of one or more bio-resorbable materials. In one variation, the material is selected to be reduced entirely volume, or at least by at least 90%, in less than 60 days, less than 30 days, less than 10 days or less than 5 days.

Figure 4A:
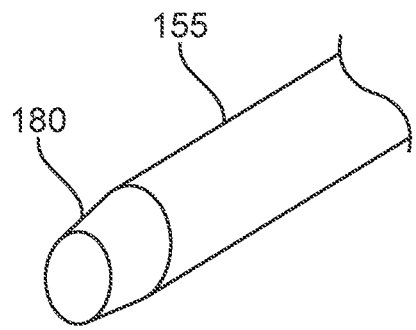
FIG. 4A is a view of a blade edge of an outer sleeve of the type shown in FIG. 3.
Figure 4B:
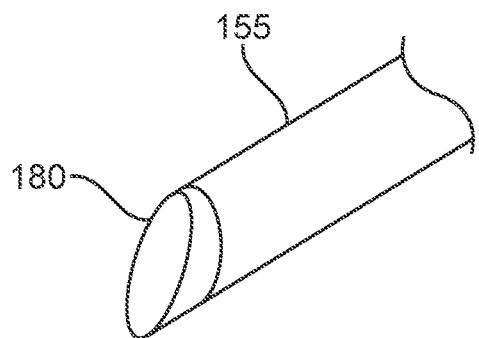
FIG. 4B is a view of another variation of a blade edge of an outer sleeve of the type shown in FIG. 3.
Figure 4C:
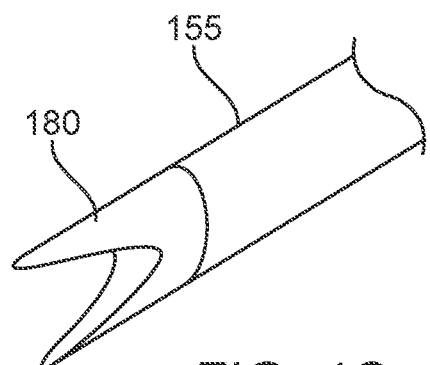
FIG. 4C is a view of another variation of a blade edge of an outer sleeve.

FIGS. 4A-4C illustrate different configurations of blade edges 180 that may be used. In one variation, the blade edge 180 is formed independent of outer sleeve 155 and then bonded to the distal end of the outer sleeve with adhesives, by over-molding or any other suitable process. In one variation, the outer sleeve 155 can be fabricated by depositing a thin parylene coating on a stretchable mandrel (e.g., a copper mandrel). The parylene or a similar layer can be deposited over the mandrel and a portion of the blade edge that is treated or perforate to optimize the polymer bonding thereto. This process can be used to fabricate a very thin wall outer sleeve 155 for the distal working end 125 of the catheter. FIG. 4A shows a cutting blade edge that is square relative to the axis of the outer sleeve 155. FIG. 4B shows a blade edge that is angled relative to the axis of sleeve 155 and FIG. 4C shows a blade edge that has a plurality of projecting edges or serrations, which can range from two to ten or more. In use the flexible inner member 156 and notch 185 may be curved in the fallopian tube 102, so the blade edge 180 must be designed to be moved back and forth over a curved member. For this reason, and angled blade edge or serrated edge such as in FIGS. 4B and 4C may work optimally when combined with rotation.

Figure 5:
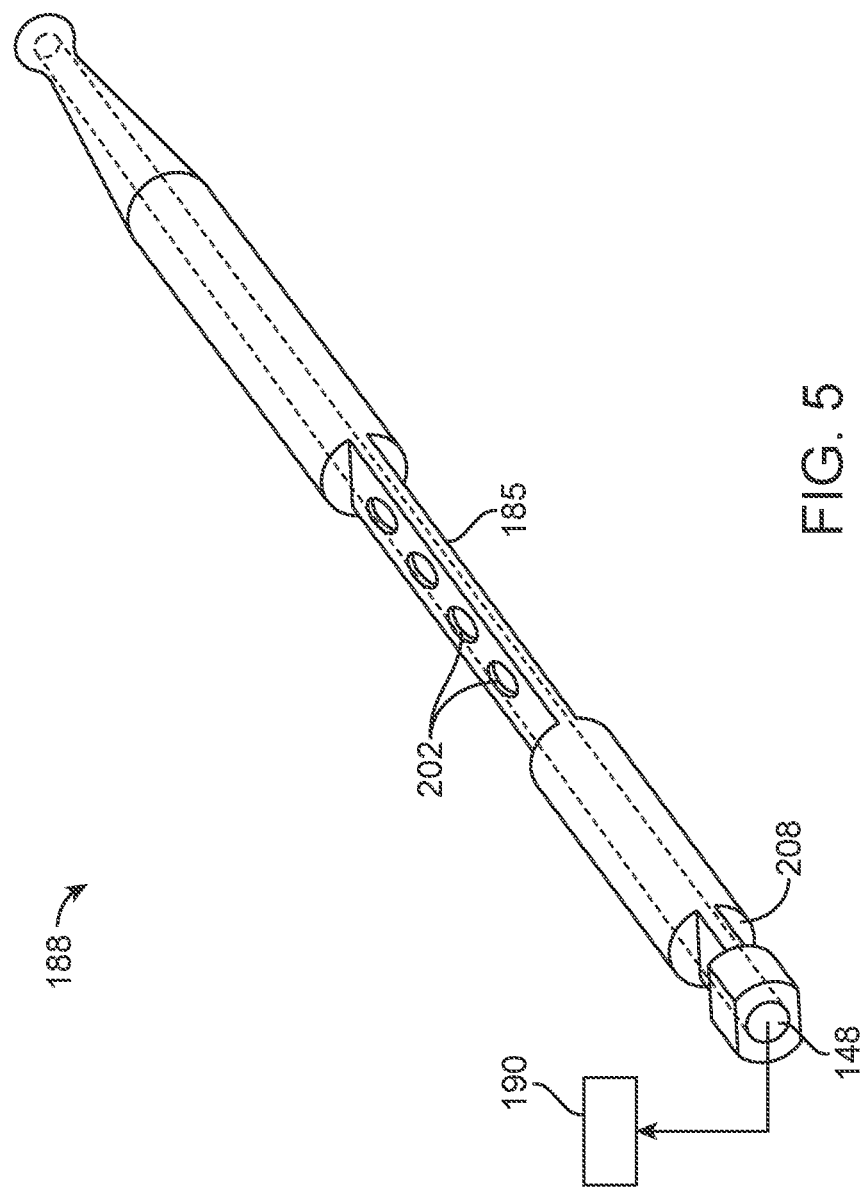
FIG. 5 is a perspective view of another variation of detachable bio-absorbable body similar to that of FIG. 3 with a region to generate a negative pressure communicating with a guidewire passageway in the body.

In another aspect of the method step shown in FIGS. 2A and 2B, the negative pressure source 190 can be actuated contemporaneous with or subsequent to the cutting step to draw blood from the cut tissue into the site. The negative pressure also can draw tissue into the recess 185 to assist in the cutting step. As can be understood from FIGS. 2A-2B, the negative pressure source 190 can be actuated manually or by controller 175 in unison with the ablative energy, or automatically timed to follow the actuation of ablative energy. The negative pressure or suction can communicate with the targeted site through the passageway 198 in the outer sleeve 155 as shown in FIGS. 2A-2B. In another variation, the negative pressure source can communicate with a guidewire passageway 148 in the catheter assembly and detachable portion 188 that extends to open ports 202 in the detachable portion as shown in FIG. 5. In any variation, the suction forces can be pulsed to sustain bleeding into the site.

FIG. 3 further illustrates that the detachable portion 188 can be locked in place with a mechanical latch or coupler 204 that allows for de-coupling from the elongate proximal body 186 of inner member 156, and in one embodiment comprises first and second opposing spring-like clasp elements 206a and 206b that can clamp on to annular groove 208 in the proximal end region 210 of the detachable portion 188. The clasp elements 206a and 206b are maintained in the clamping position to engage the annular groove 208 when the outer sleeve 155 is extended over the clasp elements. As can be understood from FIG. 3, when the outer sleeve 155 is retracted in the proximal direction to expose the coupler 204, the spring clasp elements 206a and 206b will spring outwardly to release the detachable portion 188. In other variation, the detachable portion 188 can be released from the inner member by means known in the art, such as (i) a tear-away connection that is broken by retraction of a guidewire 148 or a blade 180, (ii) a meltable polymer connection that can be melted by RF or resistive heating; (iii) a frangible connector actuated and broken by a heated shape memory (e.g, super-elastic, NiTi, etc.) element; or (iv) an electrolytic detaching mechanism as known in the art of detachable embolic coils.

Figure 6:
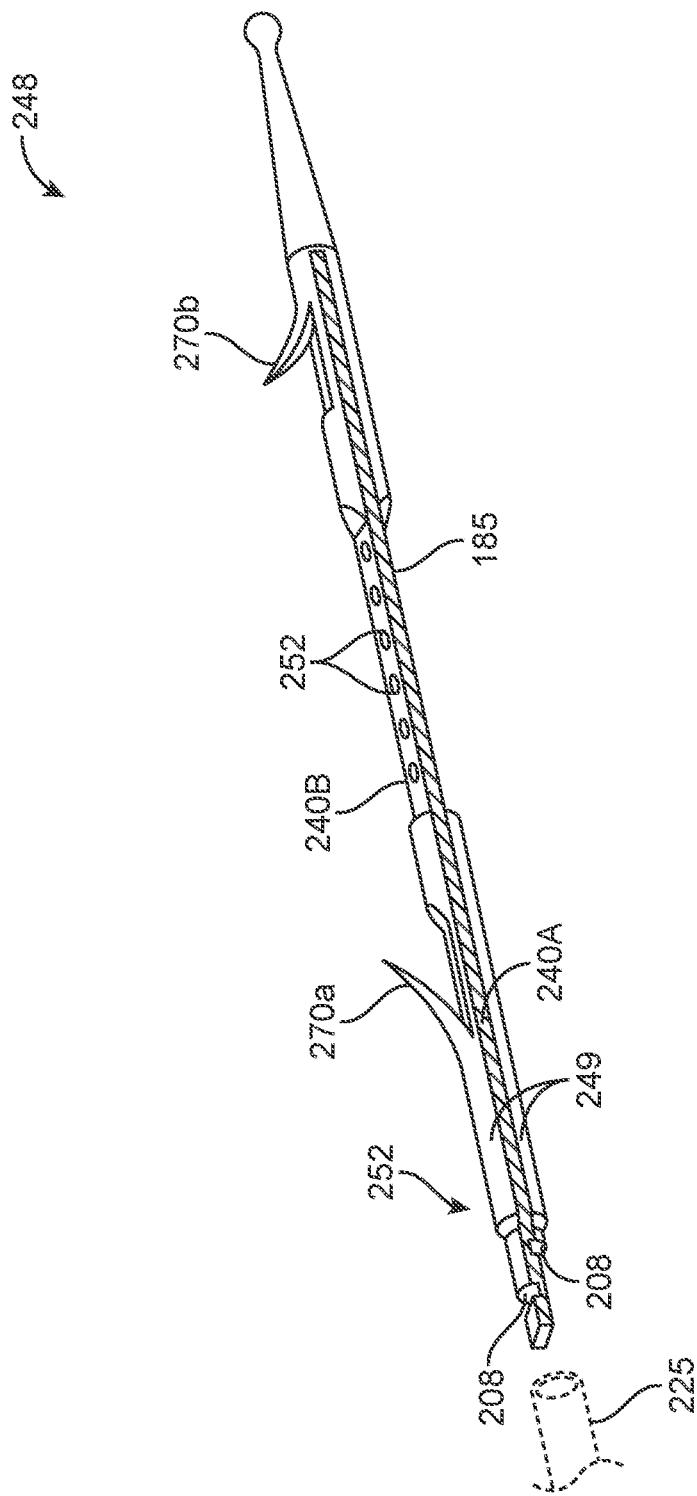
FIG. 6 is a perspective view of another variation of detachable bio-absorbable body with barb features and further showing first and second electrodes carried on opposing sides of the body.

FIG. 6 illustrates another variation of a catheter system 220 and working end 222 that uses different components of the catheter assembly to provide the various functions of the previous embodiment described above. In this variation, the outer sleeve 225 again carries a distal blade edge 180 for cutting tissue. The inner member 226 again includes a recess or notch 235 which can receive tissue that is then exposed to the blade edge 180. The working end 222 of FIG. 6 however provides the first and second opposing polarity electrodes 240A and 240B is a spaced apart configuration on the inner member. In use, the outer sleeve 225 functions (i) to cover the inner member 226 during navigation; (ii) to thereafter to move axially to cut tissue; and (iii) to maintain a latching mechanism in place as in the previous embodiment. In order to perform the ablation step, the outer sleeve 225 would be retracted to expose the electrodes 240A and 240B over a selected length, but not so far retracted so as to release the latching mechanism. The handle of the catheter assembly can be configured with locking or stop mechanism to insure that the physician retracts and reciprocates the outer sleeve within the correct parameters to sequentially expose the electrodes, then cut tissue and finally to release the detachable portion 248 of the inner member 226.

Still referring to FIG. 6, the detachable inner member portion 248 again comprises a bio-erodible or bio-absorbable material as described above, except for the first and second electrodes 240A and 240B that extend on opposing sides substantially over the length of the detachable body 248. In this variation, the electrodes on the polymer body can be fabricated by an electroless plating method, which leaves a metallic layer that is only microns in thickness. The bare polymer surfaces spaces 249 between the electrodes 240A and 240B can be provided by machining away the electroless plating material or by masking the body 248 before the electroless plating process is performed. When this variation is used, then the bio-resorbable material will disappear over a selected time interval, which will then leave the microns thick electroless plating material as a trace powder or dust. In a method of the invention, the electroless plating material can be copper which has been used for many years in intrauterine contraceptive devices. For example, a non-hormonal IUD with the brand name ParaGard® uses copper material carried on a polyethylene device. The copper causes an immune response that interferes with sperm's ability to fertilize an ovum and also may disrupt the normal division of oocytes and the formation of a fertilizable ova. This variation then would use traces of copper as an additional method of providing a contraceptive effect.

The detachable body 248 of FIG. 6 is configured to be releasable as the variation of FIG. 3, wherein first and second opposing spring-like clasp elements 206a and 206b (see FIG. 3) can clamp into notched or grooves 208 in the proximal end region 252 of the detachable body portion 248. As described above, when an outer sleeve 225 is retracted in the proximal direction to expose the coupling mechanism, the spring clasp elements 206a and 206b (see FIG. 3) will spring outwardly to release the detachable body 248. Of particular interest, the clasp elements 206a and 206b in this variation each are a component of the electrical circuit to energize the electrodes 240A and 240B, with each clasp element being coupled to a pole on the RF generator. In this variation, the polymer region in notch 185 has holes 252 therethrough or pores therein for caused rapid adhesion growth through the body 248.

Still referring to FIG. 6, this variation of detachable body 248 is further configured with at least one side-ways extending element (or barb hereafter), for example barbs 270a and 270b that can be resilient polymer elements that are configured to project outwardly after retraction of the outer sleeve 225. The barbs alternatively can be a toggle-type element that hinges to extend side-ways from the axis of the inner member 248. The purpose of the barbs is to prevent movement of the body 248 within the fallopian tube after being detached. In one variation, at least one barb is angled proximally to prevent proximal movement. In another variation, at least one barb is angled distally to prevent distal movement of the body. In a variation shown in FIG. 6, barbs angled in both directions are shown. In one variation, the barbs can be a resilient element of a bio-absorbable material from which the inner member is fabricated. Alternatively, the one or more barbs can be fabricated of a bio-erodible material such as magnesium of the type used in bio-erodible cardiovascular stents.

Figure 7A:
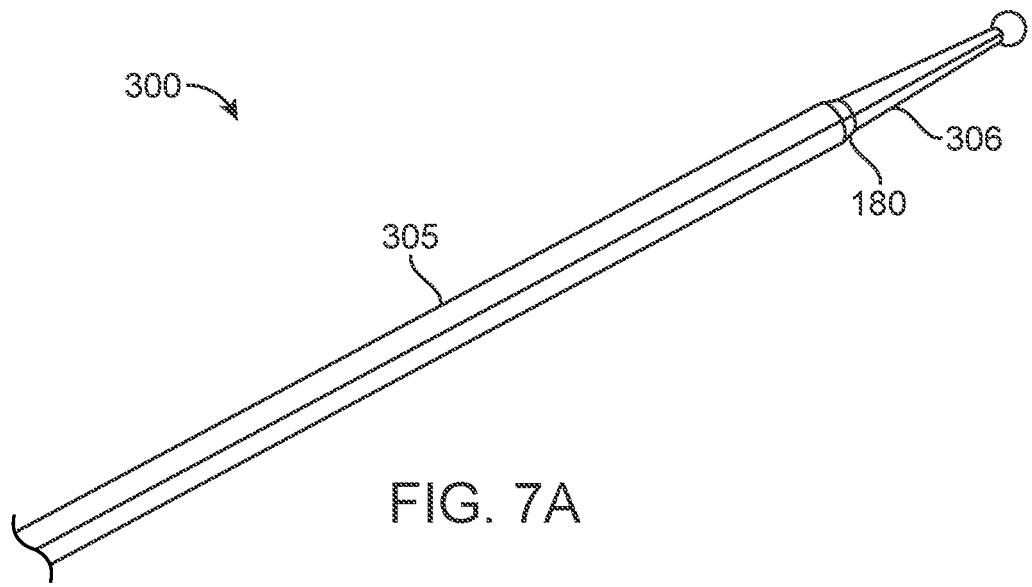
FIG. 7A is a view of another variation of catheter working end with an outer sleeve covering the inner member.
Figure 7B:
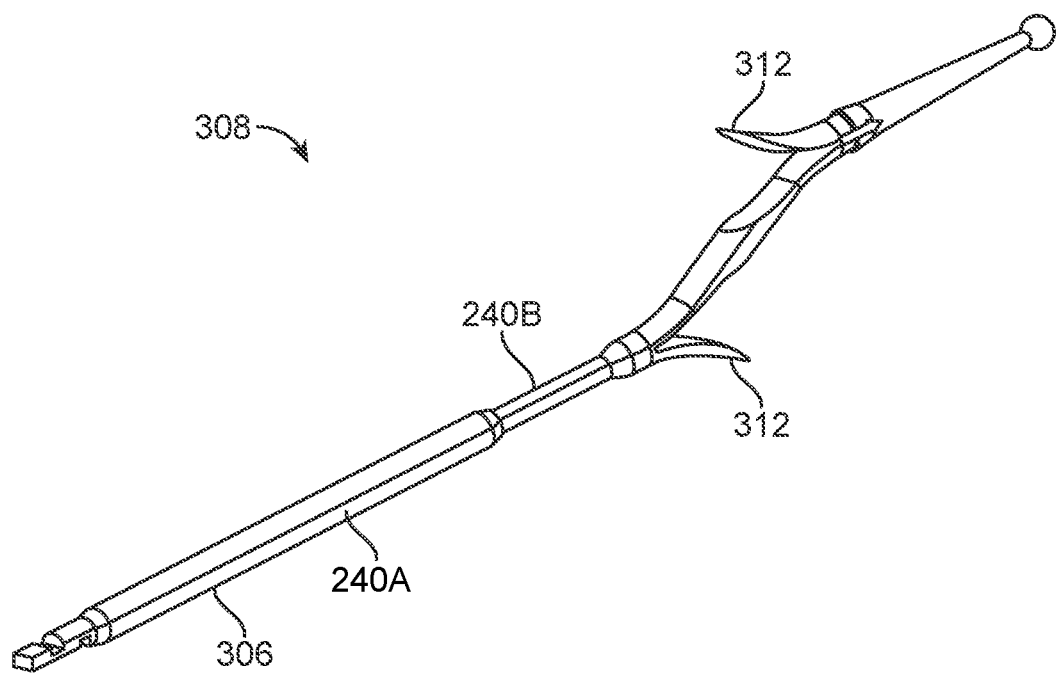
FIG. 7B is a view of the detachable bio-absorbable body of the working end of FIG. 7A showing a serpentine shaped body with barb features and further showing first and second electrodes carried on opposing sides of the body.

FIGS. 7A-7B illustrate another variation of catheter assembly 300 with outer sleeve 305 as described in previous embodiments and an inner member 306 with a detachable body 308. In this variation, the detachable body 308 has a serpentine shape which can assist in preventing dislocation of the detachable body 308 in the fallopian tube 102. This variation is further shown with barbs 312 facing both directions. In another variation (not shown) the barbs 312 can be on both sides of the notch 315 and a serpentine shape can extend through the notch and barbs 312. In this configuration, the serpentine shape can flatten the lumen of the fallopian tube to approximate the walls for faster adhesion formation across the lumen. This variation again carried electrodes 240A and 240B on opposing sides of the detachable body.

FIG. 8 is a cross-sectional view of another embodiment of a detachable body 338 that is similar to previous embodiments. In this version, the notched or reduced cross-section portion 340 is star-shaped with four projecting elements 342, but the elements 342 and flutes 344 can range in number from 3 to 12 or more.

FIG. 9 is a perspective view of another variation of a detachable body 348 that again functions as previous embodiments. In this version, the reduced cross-section portion 350 can comprise first and second bio-absorbable materials 352a and 352b that can be intermixed. The materials 352a and 352b have different rates of bio-erosion, wherein the first material can be removed rapidly, for example in 1 to 2 days, while the second material is absorbed in longer time, for example 2 to 10 days or longer. In this variation, the adhesion would form and extend through the porosities created by the disappearance of the first material while the second material would remain longer to act as a stable scaffold (e.g., with barbs as in FIGS. 6 and 7B) for tissue through-growth to occlude the fallopian tube.

In another embodiment, the detachable body of the type shown in FIG. 2B to FIG. 9 can comprise a drug-eluting material that carries a drug for enhancing the formation of an adhesion in the fallopian tube. In one variation, a growth factor may be provided, for example CTGF (connective tissue growth factor) which is available from FibroGen, Inc., 409 Illinois St., San Francisco, Calif. 94158.

While certain embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A method for occluding a fallopian tube at a targeted site, the method comprising:
   advancing a probe having a probe working end into the targeted site in the fallopian tube wherein the probe comprises a bio-erodible portion;
   activating an energy source to deliver energy through the probe working end to ablate fallopian tube tissue at the targeted site;
   cutting the ablated fallopian tube tissue at the targeted site with the probe working end; and detaching the bio-erodible portion of the probe working end to maintain coagulum accumulation at the targeted site to thereafter create an adhesion of walls of the fallopian tube.

2. The method of claim 1 wherein cutting the ablated fallopian tube tissue at the targeted site with the probe working end comprises actuating a working end mechanism of the probe working end.

3. The method of claim 1 wherein cutting the ablated fallopian tube tissue at the targeted site comprises cutting the ablated fallopian tube tissue at the targeted site to produce bleeding and the coagulum accumulation at the targeted site.

4. The method of claim 1, wherein activating the energy source to deliver energy through the probe working end to ablate the fallopian tube tissue at the targeted site further comprises ablating the mucosal layer tissue and the underlying muscle layer tissue.

5. The method of claim 1, wherein activating the energy source to deliver energy through the probe working end to ablate the fallopian tube tissue at the targeted site further comprises ablating the fallopian tube tissue over a length of 1 cm to 3 cm.

6. The method of claim 1, wherein activating the energy source to deliver energy through the probe working end to ablate the fallopian tube tissue at the targeted site further comprises ablating the fallopian tube tissue to a depth of between about 0.25 mm to 1 mm.

7. The method of claim 1, wherein cutting the ablated fallopian tube tissue at the targeted site with the probe working end further comprises cutting the ablated fallopian tube tissue pressed or drawn into one or more recesses defined along an inner member of the probe working end.

8. The method of claim 7, wherein cutting the ablated fallopian tube tissue pressed or drawn into the one or more recesses defined along the inner member of the probe working end further comprises cutting the ablated fallopian tube tissue using a blade edge at a distal end of an outer sleeve of the probe working end.

9. The method of claim 7, further comprising drawing the ablated fallopian tube tissue into the one or more recesses using negative pressure generated by a negative pressure source.

10. The method of claim 1, wherein detaching the bio-erodible portion of the probe working end to maintain the coagulum accumulation at the targeted site further comprises detaching the bio-erodible portion comprising a copper layer covering a polymeric carrier.

11. A method for occluding a fallopian tube, comprising:
advancing a probe trans-cervically to a site in the fallopian tube, the probe comprising a detachable body portion;
applying energy from the probe to ablate fallopian tube tissue at the site;
actuating a cutting mechanism of the probe to cause injury to the ablated fallopian tube tissue at the site; and
deploying the detachable body portion of the probe to stabilize coagulum at the site which thereafter facilitates adhesion of walls of the fallopian tube.

12. The method of claim 11 wherein the detachable body portion is bio-erodible.

13. The method of claim 12 wherein at least a portion of the bio-erodible body portion is configured to bio-erode from a group consisting of less than 5 days, less than 10 days, or less than 30 days.

14. The method of claim 11, wherein applying energy from the probe to ablate fallopian tube tissue at the site further comprises ablating the mucosal layer tissue and the underlying muscle layer tissue of the fallopian tube at the site.

15. The method of claim 11, wherein applying energy from the probe to ablate fallopian tube tissue at the site further comprises ablating the fallopian tube tissue over a length of 1 cm to 3 cm.

16. The method of claim 11, wherein applying energy from the probe to ablate fallopian tube tissue at the site further comprises ablating the fallopian tube tissue to a depth of between about 0.25 mm to 1 mm.

17. The method of claim 11, wherein actuating the cutting mechanism of the probe to cause injury to the ablated fallopian tube tissue at the site further comprises cutting the ablated fallopian tube tissue pressed or drawn into one or more recesses defined along an inner member of the probe.

18. The method of claim 17, wherein cutting the ablated fallopian tube tissue pressed or drawn into the one or more recesses defined along the inner member of the probe further comprises cutting the ablated fallopian tube tissue using a blade edge at a distal end of an outer sleeve of the probe.

19. The method of claim 17, further comprising drawing the ablated fallopian tube tissue into the one or more recesses using negative pressure generated by a negative pressure source.

20. The method of claim 11, wherein deploying the detachable body portion of the probe to stabilize coagulum at the site further comprises releasing the detachable body portion comprising a copper layer covering a polymeric carrier at the site to stabilize the coagulum.

\* \* \* \* \*